United States Patent

Chamberlin

[11] B 3,985,872
[45] Oct. 12, 1976

[54] DIHYDRO-A204
[75] Inventor: James W. Chamberlin, Indianapolis, Ind.
[73] Assignee: Eli Lilly and Company, Indianapolis, Ind.
[22] Filed: Nov. 15, 1974
[21] Appl. No.: 524,179
[44] Published under the second Trial Voluntary Protest Program on January 13, 1976 as document No. B 524,179.

[52] U.S. Cl. ............................. 424/122; 260/345.7
[51] Int. Cl.² ........................................ A61K 35/00
[58] Field of Search .................. 260/345.7, 345.1; 424/122

[56] References Cited
UNITED STATES PATENTS
3,705,238  12/1972  Hamill et al. .................. 260/345.9

OTHER PUBLICATIONS

Jones et al., J. Amer. Chem. Soc., 95, 3399 (1973).

Primary Examiner—James O. Thomas, Jr.
Assistant Examiner—Nicky Chan
Attorney, Agent, or Firm—Nancy J. Harrison; Everet F. Smith

[57] ABSTRACT

Dihydro-A204, prepared by reduction of antibiotic A204I, and the physiologically-acceptable cationic salts thereof increase feed-utilization efficiency in ruminants and are anticoccidial agents.

1 Claim, 1 Drawing Figure

INFRARED ABSORPTION SPECTRUM OF DIHYDRO-A204

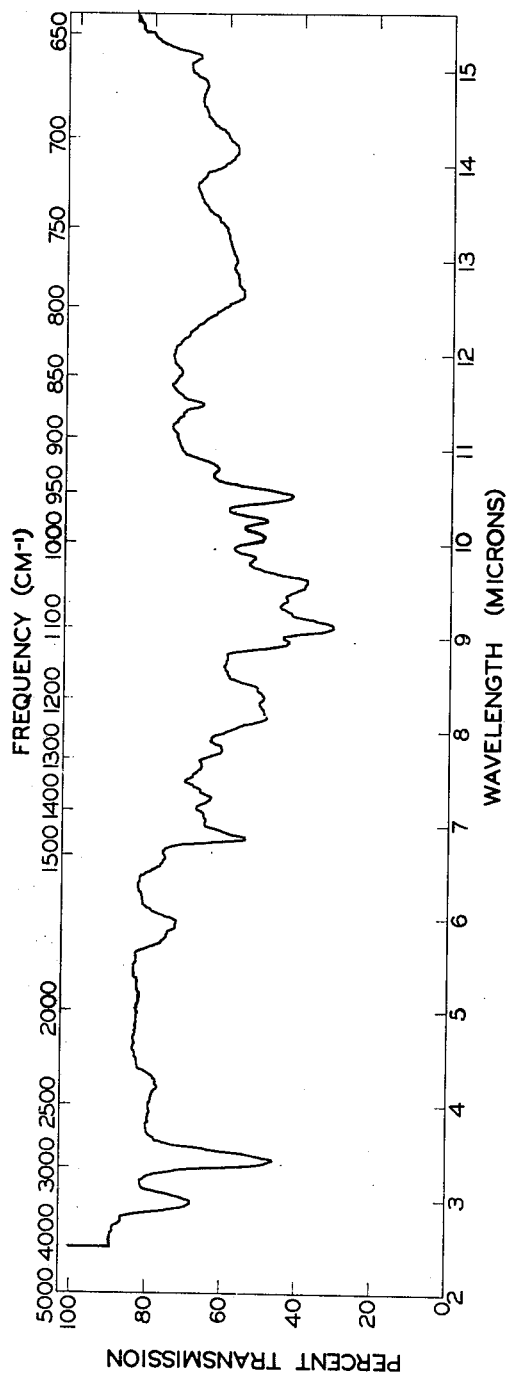

3,985,872

DIHYDRO-A204

BACKGROUND OF THE INVENTION

Field of the Invention

As world population increases, food production must also increase. In addition to being economically desirable, efficient food production is becoming essential for survival. There are, therefore, continuing efforts to find new agents which improve food production. Drugs which increase feed-utilization efficiency in ruminants are among the new agents being sought.

The mechanism for utilization of the major nutritive portion (carbohydrates) of ruminant feed is well known. Microorganisms in the rumen of the animal ferment carbohydrates to produce monosaccharides and then degrade these monosacchrides to pyruvate compounds. Pyruvates are metabolized by microbiological processes to form acetates, butyrates or propionates, collectively known as volatile fatty acids (VFA). For a more detailed discussion, see Leng in "Physiology of Digestion and Metabolism in the Ruminant," Phillipson et al., Ed., Oriel Press, pp. 408–410.

The relative efficiency of utilization of the VFA's is discussed by McCullough, Feedstuffs, June 19, 1971, page 19; Eskeland et al., J. An. Sci. 33, 282 (1971); and Church et al., "Digestive Physiology and Nutrition of Ruminants," Vol. 2, 1971, pp 622 and 625. Although acetates and butyrates are utilized, propionates are utilized with relatively better efficiency. Furthermore, when too little propionate is available, animals may develop ketosis. A beneficial drug, therefore, encourages animals to produce propionates from carbohydrates, thereby increasing carbohydrate-utilization efficiency and also reducing the incidence of ketosis.

The Prior Art

The compounds of the present invention are prepared from antibiotic A204I, which is described in U.S. Pat. No. 3,705,238.

SUMMARY OF THE INVENTION

This invention is related to dihydro-A204, a novel composition of matter prepared by mild reduction of antibiotic A204I in an inert solvent. Dihydro-A204 is separated and purified by well-known methods. The physiologically-acceptable cationic salts of dihydro-A204 are also a part of this invention and are prepared by standard chemical procedures.

Dihydro-A204 and the salts thereof are anticoccidial agents and benefit ruminants by increasing feed-utilization efficiency. This invention also relates to a method of increasing the efficiency of feed utilization in animals having a developed rumen function which comprises administering a propionate-increasing amount of dihydro-A204 or a salt thereof to such ruminants.

DESCRIPTION OF THE DRAWING

The infrared absorption spectrum of dihydro-A204 in chloroform is presented in the accompanying drawing.

DETAILED DESCRIPTION OF THE INVENTION

The biologically active agent of this invention is arbitrarily designated as dihydro-A204. The physiologically-acceptable cationic salts of dihydro-A204 are also a part of this invention. "physiologically-acceptable" salts are those salts formed from cations which do not increase the toxicity of the compound as a whole toward warm-blooded animals. Otherwise the identity of the salt-forming cation is not critical, although in some instances one may be chosen which exhibits special advantages, such as solubility, ease of purification and the like. Representative and suitable cations include the alkali metals such as sodium potassium and lithium, alkaline-earth metals such as calcium and magnesium, ammonium and the like.

The starting material in the preparation of dihydro-A204 is antibiotic A204I, which is described in U.S. Pat. No. 3,705,238. The structure of antibiotic A204I has been determined by X-ray diffraction studies [Noel D. Jones, Michael O. Chaney, James W. Chamberlin, Robert L. Hamill and Sue Chen, J. Amer. Chem. Soc. 95, 3399–3400 (1973)]. This structure is shown in Formula I:

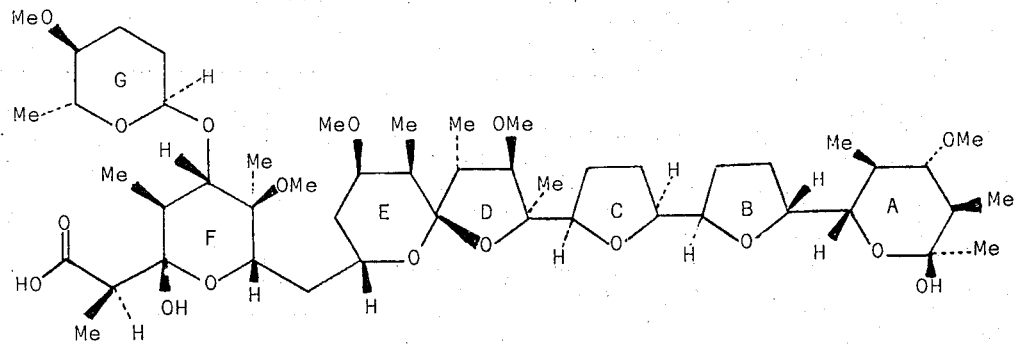

Dihydro-A204 is prepared by sodium borohydride reduction of antibiotic A204I in an inert solvent.

Although other alkali-metal borohydrides may be used to prepare dihydro-A204, sodium borohydride is preferred. A water-miscible non-hydroxylic solvent such as, for example, dioxane and sufficient water to dissolve the alkali-metal borohydride are useful solvents for this reaction. Although higher temperatures can be used, the reaction generally is complete within about 16 hours at room temperature.

In a typical workup, dihydro-A204 is separated from solid byproducts by filtration. The filtrate is diluted with water; and the diluted filtrate is extracted with, illustratively, diethyl ether. Evaporation of this ether extract gives dihydro-A204. The course of the reaction can be monitored by thin-layer chromatography.

Characteristics of Dihydro-A204

The identity of dihydro-A204 has not been established. It is believed, however, that dihydro-A204 is formed by opening the cyclic ether ring "A" of Formula I to give a diol there. As can be seen, such as opening would give rise to a new asymmetric center. There is, therefore, a probability that dihydro-A204 is a mixture of isomers.

Thin-layer chromatography (tlc) on silica gel (Merck, prepared plates) in an ethyl acetate-methanol (9:1) solvent system indicates the presence of two components with Rf values of 0.26 and 0.33 (developed by spraying with sulfuric acid and heating). Using the same tlc system, antibiotic A204I has an Rf value of 0.53.

Dihydro-A204 is a white amorphous solid. Partial elemental analysis of dihydro-A204 gave the following percentage composition: carbon, 63.64 and hydrogen, 9.11. These values correlate with the theoretical percentage compositions of carbon, 63.56, and hydrogen, 9.32, for empirical formula $C_{50}H_{88}O_{16}$.

The infrared absorption spectrum of dihydro-A204 in chloroform is shown in the accompanying drawing. The following distinguishable absorption maxima are observed: 2.96, 3.40, 5.78 (strong), 5.95, 6.87, 7.30, 7.83, 9.00 (strong), 9.13, 9.42, 9.58, 9.87, 10.10, 10.25, 10.53, and 10.80 microns. The molecular weight of dihydro-A204, as determined by the osmometric method, is 944.

Electrometric titration of dihydro-A204 is 66 percent aqueous dimethylformamide shows the presence of one titratable group having a $pk_a$ of about 5.45.

The nuclear magnetic resonance spectrum of dihydro-A204 showed the following characteristics: ($CDCl_3$) δ 3.30, 3.36, 3.43, 3.46 ($CH_3O$), 4.80 (-CH-O-) ppm.

Dihydro-A204 is soluble in diethyl ether, dimethylformamide, dimethyl sulfoxide, esters such as methyl acetate, ethyl acetate, amyl acetate and the like; ketones such as acetone, methyl ethyl ketone and methyl isobutyl ketone; halogenated hydrocarbons such as chloroform, carbon tetrachloride, and dichloroethylene; aromatic hydrocarbons such as benzene, toluene and the xylenes; and alcohols such as methanol, ethanol, isopropanol and tert-butanol. Dihydro-A204 is insoluble in water.

Dihydro-A204 and the salts thereof improve feed utilization in ruminants which have a developed rumen function. Young ruminants, basically those still unweaned, function as monogastric animals. As young ruminants begin to eat solid food, the rumen function begins to develop, and the microbiological population of the rumen begins to increase. After the animal has eaten solid feed for a time, its rumen function reaches full development and continues to operate throughout the animal's life. Some economically important ruminant animals are cattle, sheep and goats.

Dihydro-A204 or a slat thereof is typically effective in increasesing the efficiency of feed utilization when administered to ruminants orally at rates of from about 0.25 to about 12.5 mg/kg/day. Most beneficial results are achieved at rates of from about 0.5 to about 7.5 mg/kg/day. A preferred method of administering the compounds of the present invention is by mixing them with the animals' feed; however, they can be administered in other ways, for example, tablets, drenches, boluses, or capsules. Formulation of these various dosage forms can be accomplished by methods well known in the veterinary pharmaceutical art. Each individual dosage unit should contain a compound of this invention in a quantity directly related to the proper daily dose for the animal to be treated.

The ability of the compounds of this invention to increase feed-utilization efficiency in ruminants is illustrated by the following in vitro test:

Method

Rumen fluid is obtained from a steer with a surgically-installed fistula opening into the rumen. The steer is maintained on a high-grain ration, the composition of which follows:

| | |
|---|---|
| 69.95% | coarse ground corn |
| 10.00% | ground corncobs |
| 8.00% | soybean meal (50% protein) |
| 5.00% | alfalfa meal |
| 5.00% | molasses |
| 0.60% | urea |
| 0.50% | dicalcium phosphate |
| 0.50% | calcium carbonate |
| 0.30% | salt |
| 0.07% | vitamins A and $D_2$ premix* |
| 0.05% | vitamin E premix** |
| 0.03% | trace mineral premix*** |

* Containing per pound: 2,000,000 I.U. of vitamin A; 227,200 I.U. of vitamin $D_2$ and 385.7 g of soybean feed with 1% oil added
** Corn distillers dried grains with solubles containing 20,000 I.U. of d-alpha tocopheryl acetate per pound
***Containing manganous oxide, potassium iodide, cobalt carbonate, copper oxide and zinc sulfate A sample of rumen fluid is strained through four layers of cheesecloth, and the filtrate is collected. The particulate matter retained by the cheesecloth is resuspended in enough physiological buffer to return it to the original volume of the rumen fluid, and this suspension is strained again. The buffer used has the following composition:

| g/l. | Ingredient |
|---|---|
| 0.316 | $Na_2HPO_4$ |
| 0.152 | $KH_2PO_4$ |
| 2.260 | $NaHCO_3$ |
| 0.375 | KCl |
| 0.375 | NaCl |
| 0.112 | $MgSO_4$ |
| 0.040 | $CaCl_2.2H_2O$ |
| 0.008 | $FeSO_4.7H_2O$ |
| 0.004 | $MnSO_4.H_2O$ |
| 0.004 | $ZnSO_4.7H_2O$ |
| 0.002 | $CuSO_4.5H_2O$ |
| 0.001 | $CoCl_2.6H_2O$ | as described by Cheng et al. in *J. Dairy Sci.* 38, 1225, (1955).

The two filtrates are combined and allowed to stand until particulate matter separates to the top. The clear layer is separated, is diluted with the same buffer (1:1) and then is adjusted to between pH 6.8–7.0.

The diluted rumen fluid (10 ml) is placed in a 25-ml flask with 40 mg of the above-described feed, an additional 5 mg of soybean protein, and the compound to be tested. Four replicate flasks are used per treatment. Two sets of four control flasks each are also employed. A zero-time control and an incubated 16-hour control are used. All test flasks are incubated for 16 hours at 38°C. After incubation the pH is measured, and 25 percent metaphosphoric acid (2 ml) is added to each flask. The samples are allowed to settle, and the supernatant is analyzed by gas chromatography for propionate, acetate, and butyrate compounds. Active compounds significantly increase propionate production over that of controls.

Test-compound results are statistically compared with control results. Table I below shows the ratio of volatile-fatty-acid concentrations in dihydro-A204-treated flasks to concentrations in control flasks in two separate sets of tests.

TABLE I

FEED-UTILIZATION-EFFICIENCY ACTIVITY OF DIHYDRO-A204

| Test | mcg/ml diluted rumen fluid | Acetate | Propionate | Butyrate | Total VFA |
|---|---|---|---|---|---|
| I | 25 | 0.90 | 1.66 | 0.79 | 1.03 |
|  | 5 | 0.95 | 1.24 | 0.93 | 1.01 |
|  | 1 | 0.98 | 0.95 | 1.06 | 0.91 |
| II | 25 | 0.93 | 1.49 | 0.81 | 1.07 |
|  | 5 | 0.98 | 1.13 | 0.93 | 1.01 |
|  | 1 | 0.99 | 0.98 | 1.01 | 0.97 |

Decreased toxicity is an important advantage provided by the compounds of the present invention. The acute toxicity of dihydro-A204, administered orally to mice and expressed as $LD_{50}$, is 28 mg/kg. In contrast, two corresponding acute toxicity studies on antibiotic A204I gave $LD_{50}$ 's of 8.3 and 12.3 mg/kg.

Dihydro-A204 and the salts thereof are also anticoccidial agents. For example, when used in the control of coccidiosis in poultry, a nontoxic, anticoccidial amount of dihydro-A204 or a salt thereof is administered to birds, preferably orally on a daily basis. Although a variety of factors must be considered in determining the appropriate concentration of dihydro-A204 or dihydro-A204 salt used, the rate of administration will be generally in the range of from about 0.001 to about 0.05 percent by weight of unmedicated feed, and preferably in the range of 0.005 to 0.02 percent. The dihydro-A204 compound can be administered in many ways, but it is most conveniently supplied with a physiologically-acceptable carrier. preferably the feed or water ingested by the birds.

The anticoccidial activity of dihydro-A204 is further illustrated by tests involing *Eimeria tenella* in chickens.

Method

For these studies, groups of five 7-day-old chicks were fed a mash diet containing dihydro-A204 uniformly dispersed therein. After having been on this ration for 48 hours, each bird was inoculated with sporulated oocysts of *Eimeria tenella*.

Other groups of five 7-day-old chickens were fed a mash diet which did not contain dihydro-A204. Some of these groups were also inoculated with *E. tenella* after 48 hours and served as infected controls. Other of these groups were not inoculated with *E. tenella* and served as normal controls. The results of treatment were evaluated 7 days after inoculation. The birds were weighed, sacrificed and examined for evidence of coccidial lesions. Coccidial involvement was expressed on an arbitrary scale, increasing from zero (no evidence of coccidiosis) to four (maximum involvement for *E. tenella*). The percent reduction in lesion score is calculated by subtracting the average lesion score of the treated group from the average lesion score of the infected control group, dividing this difference by the average lesion score of the infected control group, and multiplying the quotient by 100.

The percent weight gain is calculated using the weight gain of normal controls as 100 percent.

The results of two sets of tests are shown in Table II.

TABLE II

ACTIVITY OF DIHYDRO-A204 AGAINST *E. tenella* IN BROILER COCKERELS

| Treatment | % in Diet | % Mortality | % Weight gain | Average Cecal Lesion Score | % Reduction Lesion Score |
|---|---|---|---|---|---|
| Dihydro-A204[1] | .0132 | 0 | 76 | 0 | 100 |
| " | .0088 | 0 | 104 | 0 | 100 |
| " | .0044 | 0 | 97 | .5 | 88 |
| " | .0022 | 0 | 55 | 3.3 |  |
| Infected Controls[2] |  | 20 | 51 | 4.0 |  |
| Dihydro-A204[1] | .0044 | 0 | 92 | 1.6 | 60 |
|  | .0022 | 6.7 | 56 | 3.7 |  |
| Infected Controls[1] |  | 26.7 | 42 | 4.0 |  |

[1]Three pens of five birds each
[2]Four pens of five birds each

The following examples are provided to more fully illustrate the preparation of the compounds of this invention.

EXAMPLE 1

Preparation of Dihydro-A204

Sodium borohydride (0.30 g) was added with stirring to a solution of antibiotic A204I (1.0 g) in dioxane (50 ml). An amount of water sufficient to dissolve the sodium borohydride was added dropwise. The solution was stirred overnight at room temperature. The precipitate which formed during this time was removed by filtration. the filtrate was diluted with water, and the diluted filtrate was extracted three times with diethyl ether. The combined ether extracts were washed twice with water, were dried ($Na_2SO_4$) and were evaporated to dryness under vacuum to give 0.83 g of dihydro-A204.

EXAMPLE 2

Preparation of Dihydro-A204 Sodium Salt

Dihydro-A204 (200 mg), prepared as described in Example 1, was dissolved in 50 ml of methanol-water (3:1). The pH of this solution was adjusted to pH 10.7 by the addition of 0.1 N sodium hydroxide. The resulting solution was evaporated to dryness to give the sodium salt of dihydro-A204: infrared spectrum (CHCl$_3$) $\gamma_{max}$ 3.0 (OH), 5.8, 6.3 (CO$_2^-$) μ.

I claim:
1. Dihydro-A204, which is a white amorphous solid, soluble in diethyl ether, dimethylformamide, dimethyl sulfoxide, methyl acetate, ethyl acetate, amyl acetate; sulfoxide, acetone, methyl ethyl ketone, methyl isobutyl ketone; chloroform, carbon tetrachloride, dichloroethylene; benzene, toluene, xylene, methanol, ethanol, isopropanol and tert-butanol; and insoluble in water; and which has:
   a. a molecular weight, as determined by the osmometric method, of 944;
   b. an approximate elemental composition of 63.64% carbon, 9.11% hydrogen and 27.25% oxygen;
   c. an empirical formula of C$_{50}$H$_{88}$O$_{16}$;
   d. an infrared absorption spectrum in chloroform with distinguishable absorption maxima at 2.96, 3.40, 5.78 (strong), 5.95, 6.87, 7.30, 7.83, 9.00 (strong), 9.13, 9.42, 9.58, 9.87, 10.10, 10.25, 10.53 and 10.80 microns;
   e. a nuclear magnetic resonance spectrum with the following characteristics: (CDCl$_3$) δ 3.30, 3.36, 3.43, 3.46 (CH$_3$O), 4.80 (-CH-O-) ppm;
   f. in 66 percent aqueous dimethylformamide, one titratable group having a pKa of about 5.45; and
   g. Rf values of 0.26 and 0.33 on silica-gel thin-layer chromatography in ethyl acetate-methanol (9:1); and which forms cationic salts, the sodium salt thereof having an infrared absorption spectrum in chloroform with absorption maxima at 3.0 (OH), 5.8, and 6.3 (CO$_2^-$) microns; or the physiologically-acceptable cationic salts thereof.

* * * * *

UNITED STATES PATENT AND TRADEMARK OFFICE
CERTIFICATE OF CORRECTION

PATENT NO. : 3,985,872
DATED : October 12, 1976
INVENTOR(S) : James W. Chamberlin It is certified that error appears in the above–identified patent and that said Letters Patent are hereby corrected as shown below:

Column 3, line 2, the last "as" should read --an--.

Column 3, line 56, "slat" should read --salt--.

Column 5, line 23, "$LD_{50}$ I $_s$" should read --$LD_{50}$'s--.

Column 7, line 9, delete "sulfoxide".

Signed and Sealed this

First Day of February 1977

[SEAL]

Attest:

RUTH C. MASON
*Attesting Officer*

C. MARSHALL DANN
*Commissioner of Patents and Trademarks*